United States Patent
Norén et al.

(10) Patent No.: US 6,754,535 B2
(45) Date of Patent: Jun. 22, 2004

(54) METHOD AND APPARATUS FOR VERIFYING EVOKED RESPONSE IN THE ATRIUM

(75) Inventors: Kjell Norén, Karolinagatan (SE); Nils Holmström, Päronvägen (SE)

(73) Assignee: St. Jude Medical AB, Järfälla (SE)

( * ) Notice: Subject to any disclaimer, the term of this patent is extended or adjusted under 35 U.S.C. 154(b) by 212 days.

(21) Appl. No.: 09/901,324

(22) Filed: Jul. 9, 2001

(65) Prior Publication Data

US 2003/0009200 A1 Jan. 9, 2003

(51) Int. Cl.⁷ .............................................. A61N 1/362
(52) U.S. Cl. .................... 607/28; 600/509; 600/547
(58) Field of Search ........................ 607/28, 9, 27; 600/509, 521, 547

(56) References Cited

U.S. PATENT DOCUMENTS 5,649,968 A  *  7/1997  Alt et al. ..................... 607/19
5,902,325 A  *  5/1999  Condie et al. ............... 607/28

FOREIGN PATENT DOCUMENTS

| EP | 0 857 493 | 1/1998 |
| EP | 0 882 469 | 6/1998 |
| EP | 1 062 974 | 6/2000 |
| WO | WO 98/25672 | 6/1998 |
| WO | WO 01/10499 | 2/2001 |

* cited by examiner

*Primary Examiner*—Kennedy Schaetzle
(74) *Attorney, Agent, or Firm*—Schiff Hardin & Waite

(57) ABSTRACT

In a method and an apparatus for verifying the occurrence of an evoked response in the atrium, following emission of a stimulation pulse to the atrium, an impedance signal is measured in a time window following the emission of the stimulation pulse. The impedance signal is high pass filtered and a characteristic of the high pass filtered impedance signal, such as its amplitude or its morphology, is compared to a predetermined criterion in a comparison unit. The occurrence of an evoked response is verified if the characteristic equals or exceeds the predetermined criterion. The occurrence of an evoked response can therefore be monitored on a beat-to-beat or pulse-to-pulse basis.

32 Claims, 6 Drawing Sheets

METHOD AND APPARATUS FOR VERIFYING EVOKED RESPONSE IN THE ATRIUM

BACKGROUND OF THE INVENTION

1. Field of the Invention

The present invention is directed to a method for verifying evoked response in the atrium, as well as to an apparatus for conducting the method.

2. Description of the Prior Art

The term "evoked response" means the electrical activation which takes place in the myocardium by a pacing pulse which is emitted by a pacemaker. The presence or occurrence of an evoked response following a pacing pulse means that the pulse was successful for its intended purpose, i.e., artificially stimulating a heartbeat. The absence of an evoked response following a pacing pulse means that one or more parameters of the pacing pulse, such as its energy content or its timing relationship to other pulses, must be adjusted. A chronic absence of evoked response can be indicative of a more serious problem, such as a failure of the electrode lead system or a dislodged electrode lead.

Verifying evoked response in the atrium following a pacing pulse presents a difficult problem. Many techniques are known for verifying capture, which is the successful depolarization and contraction of a cardiac chamber caused by a stimulation pulse from a pacemaker. One-to-one capture occurs when each pacemaker output pulse results in a contraction of the appropriate chamber. A conventional autocapture system verifies capture on a beat-by-beat basis. It would be advantageous to be able to verify evoked response in the same or a similar manner so that an evoked response system could be used in conjunction with a conventional autocapture system.

SUMMARY OF THE INVENTION

It is an object of the present invention to provide a method and an apparatus for verifying evoked response on a beat-by-beat basis.

It is also an object of the present invention to provide a method and apparatus for verifying evoked response which can be used in conjunction with a conventional autocapture system.

The above objects are achieved in accordance with the principles of the present invention in a method and an apparatus for verifying evoked response wherein a conventional bipolar pacing electrode is placed in the right atrium, and impedance in the right atrium is measured between the tip and the ring of the electrode. The measured impedance is processed within a time window after emission of a stimulation pulse, and evoked response is verified if the processed impedance signal satisfies a predetermined criterion within the time window. The predetermined criterion can be a comparison of the processed impedance signal, or a characteristic thereof, with a threshold. Alternatively, the predetermined criterion can be comparison of the morphology (i.e. signal curve shape) of the processed impedance signal with a stored morphology (template). In an embodiment of the invention, the time window for making the impedance measurement is determined in dependence on the time that the stimulation pulse to the right atrium is emitted, in order to save battery current. The frequency range of the measured impedance is preferably approximately 50 Hz. The measured impedance signal can be high pass filtered, to obtain the typical delta Z signal that is used for capture verification. Particularly if the predetermined criterion is a morphology comparison, a typical bandwidth for the impedance signal can be between 2 Hz and 40 Hz, with the detection window starting 40 ms after the stimulation pulse and ending at 160 ms after the stimulation pulse. In another embodiment, the bandwidth can be between 4 Hz and 40 Hz and the time window can start 80 ms after the stimulation pulse and end at 180 ms after the stimulation pulse.

In an embodiment, the sensing amplifier, and other components in the impedance signal processor, can be enabled by the pacing logic to operate in the aforementioned time window, and this enabling can be varied dependent on the pacing rate. Additionally or alternatively, the high pass filter can be operated by the pacing logic to select a bandwidth for processing the impedance signal, and this selection also can be varied dependent on the pacing rate.

The simplest algorithm for determining whether the predetermined criterion has been satisfied is to use the amplitude of the processed impedance signal and to compare this amplitude to a simple amplitude threshold, with the processed impedance signal being set to zero at the start of the time window. In order to suppress noise, the impedance signal can be integrated within the time window. An evoked response is then verified if the processed signal reaches a predetermined threshold.

As noted above, another alternative is to employ a morphology comparison. For this purpose, in an embodiment, a morphology comparator can have data representing a curve stored therein, with the curve of the incoming impedance signal being compared to the stored curve. In a further embodiment, a number of different curves (templates) can be stored in a temp late memory, to which the morphology comparator has access. One of the stored curves can be selected by the pacing logic, dependent on pacing rate and/or other pacing conditions, with the selected curve end being supplied to the morphology comparator for comparison with the processed impedance signal.

DESCRIPTION OF THE PREFERRED EMBODIMENTS

Figure 1:
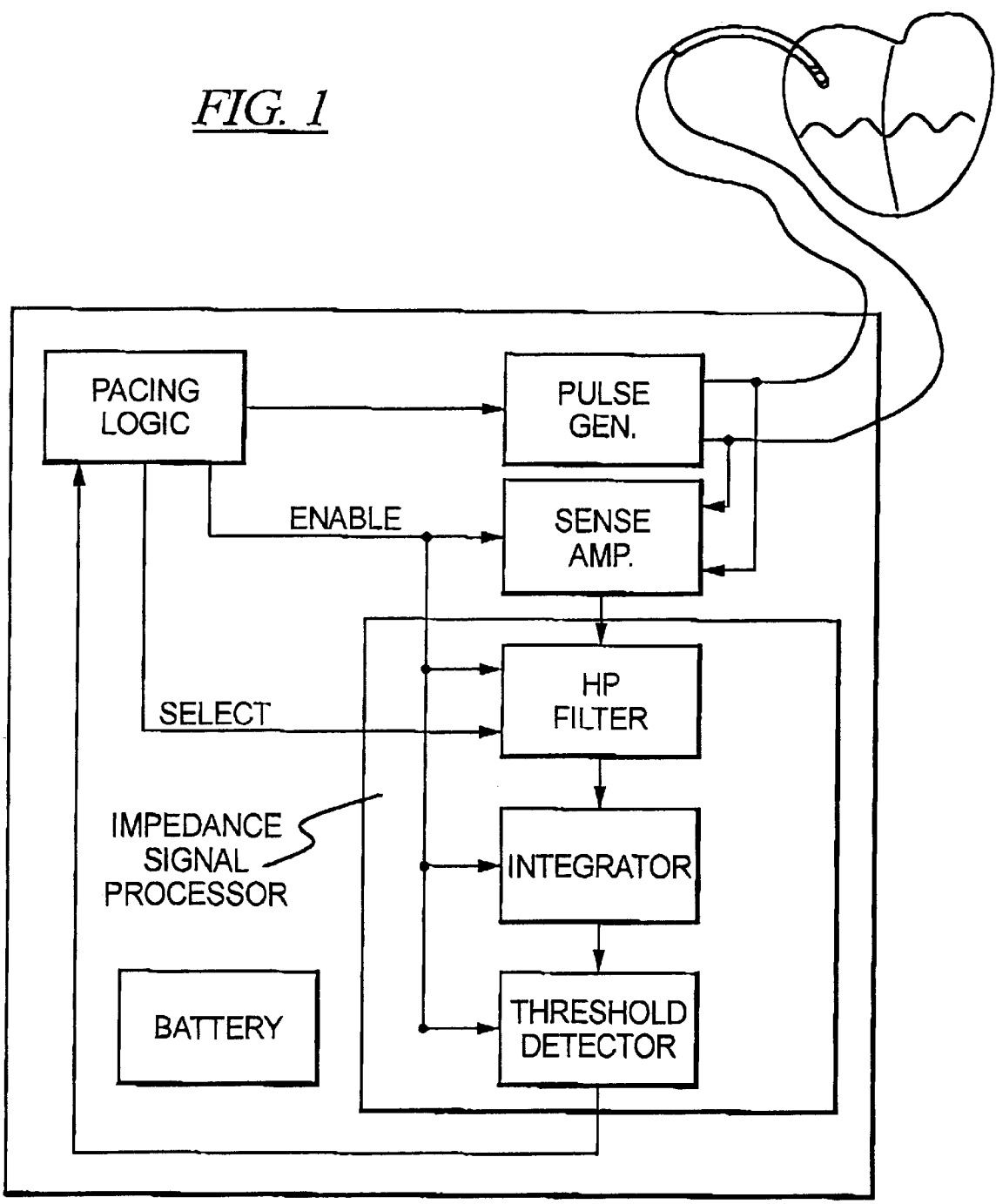
FIG. 1 is a block diagram of a pacemaker with evoked response verification capability, constructed and operated in accordance with the principles of the present invention, having an impedance signal processor in a first embodiment of the invention.

The pacemaker shown in FIG. 1 has an electrode lead system which, at a minimum, includes an electrode lead adapted for implantation in the right atrium of the heart of a patient. The electrode lead is a conventional bipolar lead, having an electrode tip and a ring electrode. Other leads may be present, such as a ventricular lead for dual chamber pacing, however, for explaining the impedance sensing in accordance with the invention, as it relates to evoked response detection, only the atrial lead needs to be considered.

The electrode lead is connected to a pulse generator which is operated by pacing logic in a conventional manner to deliver a therapy regimen, including pacing pulses, each having an energy content and each being in timed relation to other pulses, for artificially stimulating the heart. Ideally, each pacing pulse will successfully stimulate the heart, so that a polarization/depolarization cycle occurs, with an associated contraction of the heart muscle.

In order to confirm, on a beat-by-beat (or pulse-by-pulse) basis that an evoked response has, in fact, occurred in the heart, impedance is detected in the right atrium of the heart by a measurement made between the aforementioned tip electrode and ring electrode. The impedance measurement is made by a sense amplifier, which is also connected to the electrode lead, and which is enabled (activated) for a specified time window by receipt of an enable signal from the pacing logic. The time window is started by the pacing logic at a predetermined time after emission of the stimulation pulse by the pulse generator. Since the pacing logic triggers the emission of a stimulation pulse from the pulse generator, the pacing logic "knows" when the pacing pulse was emitted. The time window ends at a further predetermined time after the emission of the stimulation pulse.

The impedance signal received by the sense amplifier is supplied to an impedance signal processor, and initially therein is high pass filtered in a high pass filter, which is also enabled during the aforementioned time window by the enable signal from the pacing logic. The upper frequency of the measured impedance signal will be approximately 50 Hz, which is well within the requirements for conventional types of pacemaker signal processing. By high pass filtering the incoming impedance signal, the so-called delta Z signal is obtained.

The bandwidth of the high pass filter can be selected by a select signal from the pacing logic supplied to the high pass filter. The selection of the frequency range of the high pass filter is more useful in connection with the morphology comparison embodiments described in connection with FIGS. 2 and 3 below, but it may also be useful in the embodiment of FIG. 1, wherein threshold detection is employed.

The selection of the bandwidth for the high pass filter can be associated with a particular detection window. For example, the pacing logic can set the bandwidth as 2–40 Hz, for a detection window that starts at 40 ms after the stimulation pulse and ends at 160 ms after the stimulation pulse. Another example is to select the bandwidth as 4–40 Hz, and to employ a detection window which begins 80 ms after the emission of the stimulation pulse and ends at 180 ms after the emission of the stimulation pulse.

It is also possible to select and alter one or both of these parameters dependent on the pacing rate. For that purpose, the pacing logic can be supplied with conventional information for setting and adjusting the pacing rate, including physiological sensors for operating in a rate responsive mode. Such sensors and circuitry are well-known to those of ordinary skill in the art and need not be described in detail herein.

The output of the high pass filter can be supplied, in the embodiment of FIG. 1, directly to a threshold detector. The occurrence of an evoked response is verified if the high pass filtered impedance signal exceeds a predetermined threshold. For suppressing the effect of noise, an integrator can be connected between the high pass filter and the threshold detector, with the high pass filtered impedance signal being integrated therein. The threshold detector then verifies that an evoked response has occurred if the integrated, high pass filtered impedance signal exceeds a predetermined threshold. In each case, the threshold detector emits an output signal to inform the pacing logic if and when verification of an evoked response is made.

All components in the pacemaker are powered by a battery. For clarity, electrical connections from the battery to each of the components are not shown in FIG. 1, since these types of connections are well-known to those of ordinary skill in the art. In order to conserve battery power, the threshold detector and the integrator (if used) are also enabled to operate only within the time window by the enable signal from the pacing logic.

Figure 2:
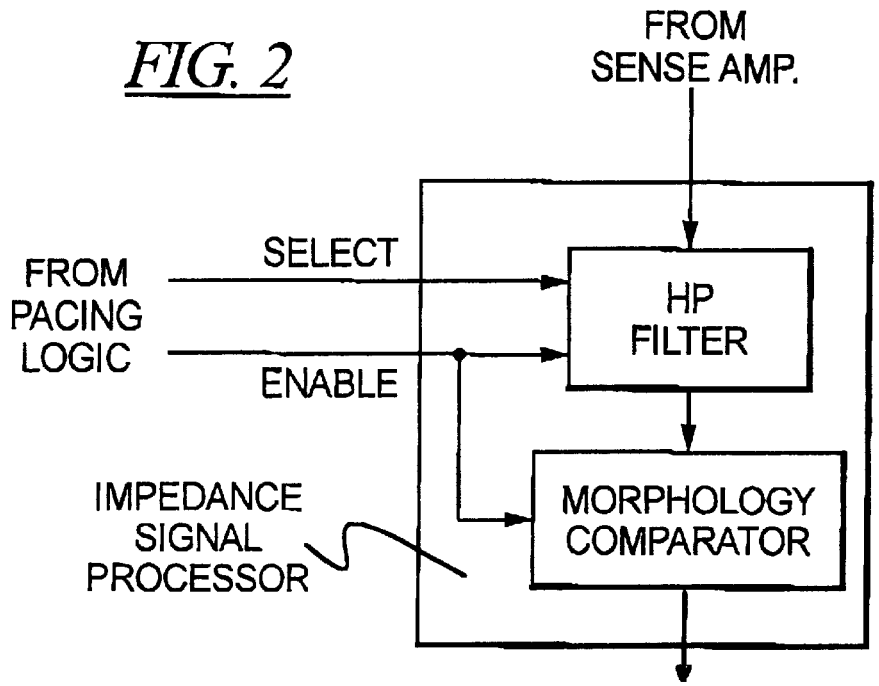
FIG. 2 is a block diagram of a second embodiment of an impedance signal processor in accordance with the invention.
Figure 3:
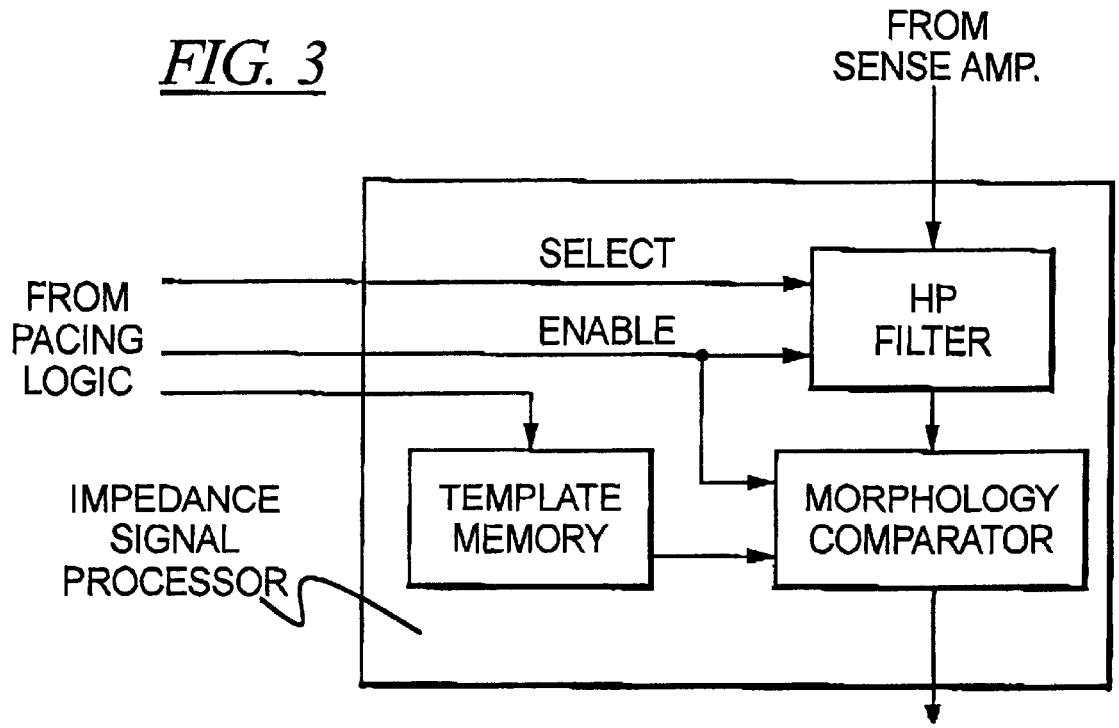
FIG. 3 is a block diagram of a third embodiment of an impedance signal processor in accordance with the invention.

In the embodiment of the impedance signal processor shown in FIG. 2, the high pass filtered impedance signal is supplied to a morphology comparator. Morphology comparators are known in the art, and either mathematically or graphically compare a curve (or a mathematical representation thereof) to a stored curve template, and produce an output signal dependent on the degree of correlation. The degree of correlation which triggers an output signal can be selected. In the embodiment of FIG. 2, the occurrence of an evoked response is verified if the curve of the high pass filtered impedance signal matches a stored curve or template to a degree specified by a predetermined correlation factor. In the embodiment of FIG. 3, the morphology comparator has access to a template memory, wherein a number of templates or curves are stored. The curves can be experimentally obtained from the patient in whom the pacemaker is implanted or can be predetermined curves obtained from a patient population. The curves represent typical impedance signal curves which are found to occur in the context of various pacing regimens and patient pathologies. Depending on the prevailing conditions, a signal from the pacing logic to the template memory selects one of these curves for use by the morphology comparator in the comparison to the high pass filtered impedance signal. Again, the presence of an evoked response is verified if the comparison results in a correlation which is at or exceeds a predetermined correlation factor.

In each of the embodiments of FIG. 2, the morphology comparator supplies an output signal to the pacing logic to inform the pacing logic that an evoked response has occurred.

Figure 4:
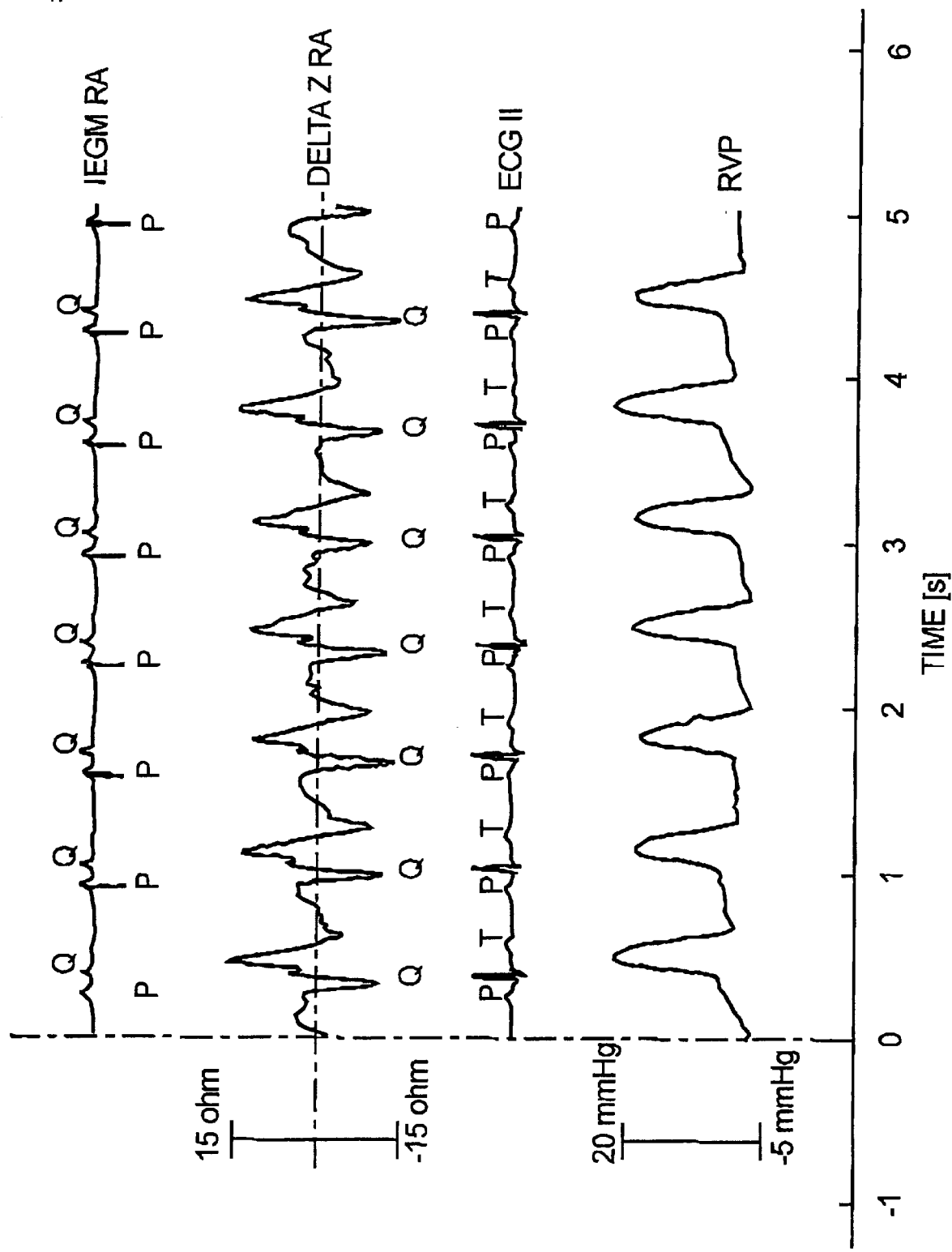
FIG. 4 shows various signal curves obtained in accordance with the invention in a first experimental setup.

FIG. 4 shows typical signals of the type conventionally obtained and associated with pacing monitoring. The signals shown in FIG. 4 are the IEGM in the right atrium (RA), the delta Z signal from the right atrium, shown in a scale between −15 ohm and 15 Ohm, the ECG II signal, and a signal representing right ventricular pressure, shown in a scale between −5 mmHg and 20 mmHg.

Figure 5:
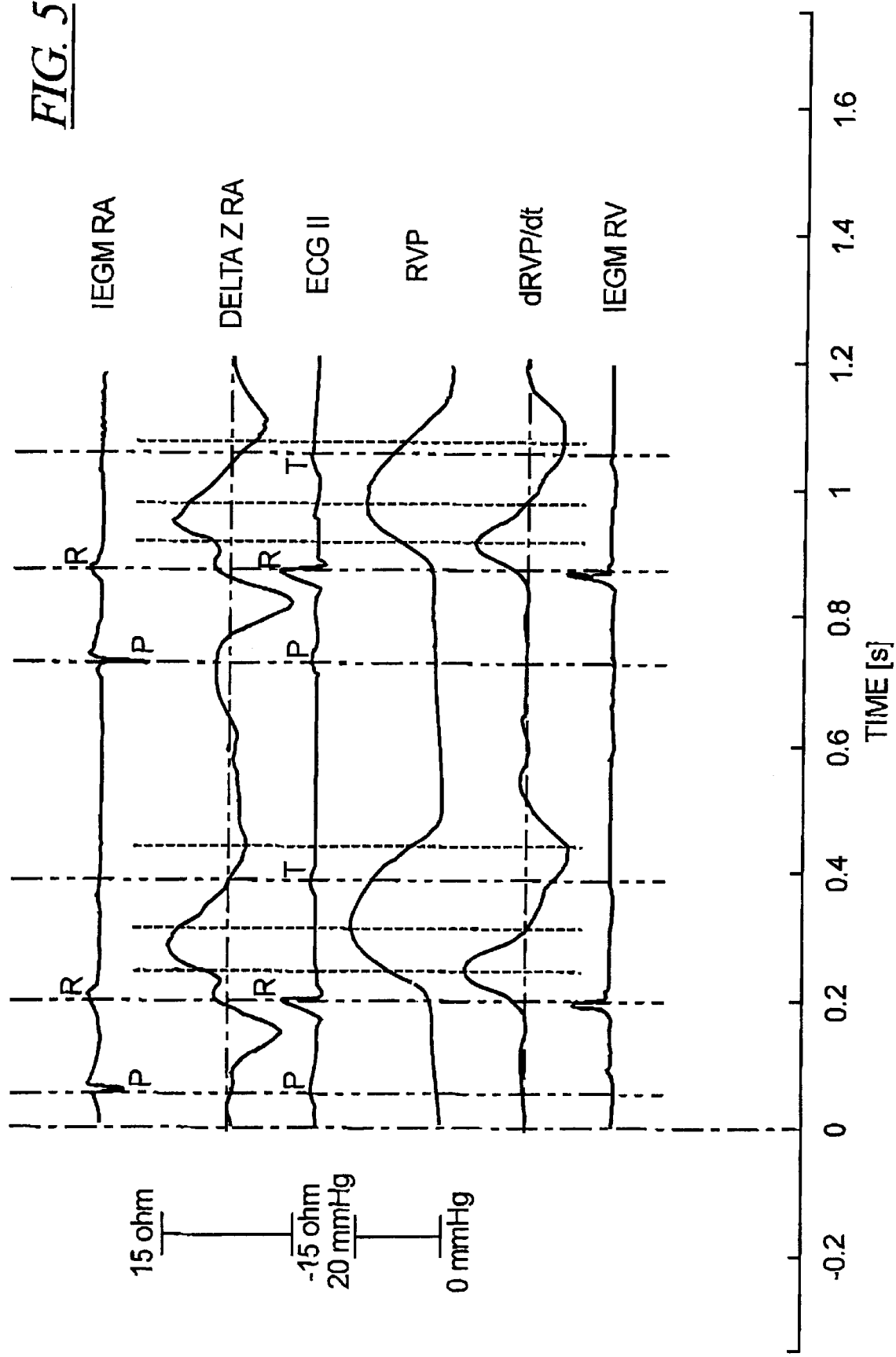
FIG. 5 shows various signal curves obtained in accordance with the invention in a second experimental setup.

FIG. 5 shows examples of such signals with an expanded time scale, and additionally includes dRVP/dt and the right ventricular (RV) IEGM signal. In this example, delta Z was measured with an excitation current of 10 $\mu$A at 4 kHz. The bandwidth for delta Z is 0.5–40 Hz. It is apparent that each P-wave is followed by a strong negative deflection in the impedance.

Figure 7:
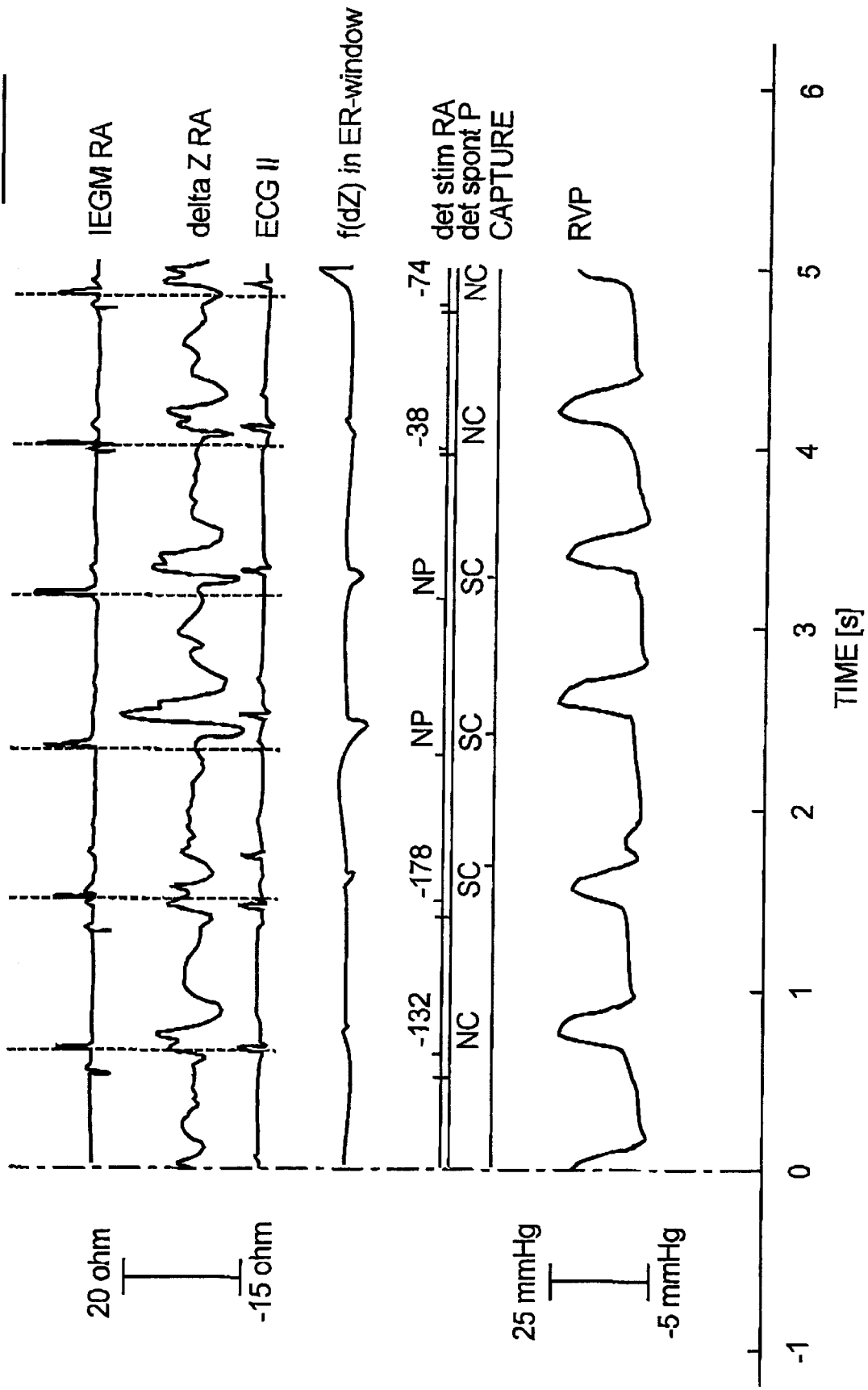
FIG. 7 shows various signal curves obtained in accordance with the invention in a fourth experimental setup.

FIG. 7 illustrates capture verification according to the invention. The right atrium is paced at a lower rate than the spontaneous P-wave rate. The delta Z bandwidth is 2–40 Hz, and the detection window is between 20 ms and 160 ms following the emission of each pulse. The impedance signal was integrated within this time window. FIG. 7 also shows the detection of stimulation in the right atrium and the detection of a spontaneous P-wave. The designation NP indicates that there was no P-wave before the stimulation pulse, SC indicates stimulated capture and NC indicates no capture. The numerical indications indicate the number of milliseconds that a P-wave occurred before a stimulation pulse.

As can be seen, for three of the stimulated beats, the stimulation pulse was preceded by a spontaneous P-wave and the stimulation occurred in the refractory period of the right atrium. In the fourth case, capture occurred when the P-wave preceded stimulation by 178 ms (non-refractory atrium).

Figure 6:
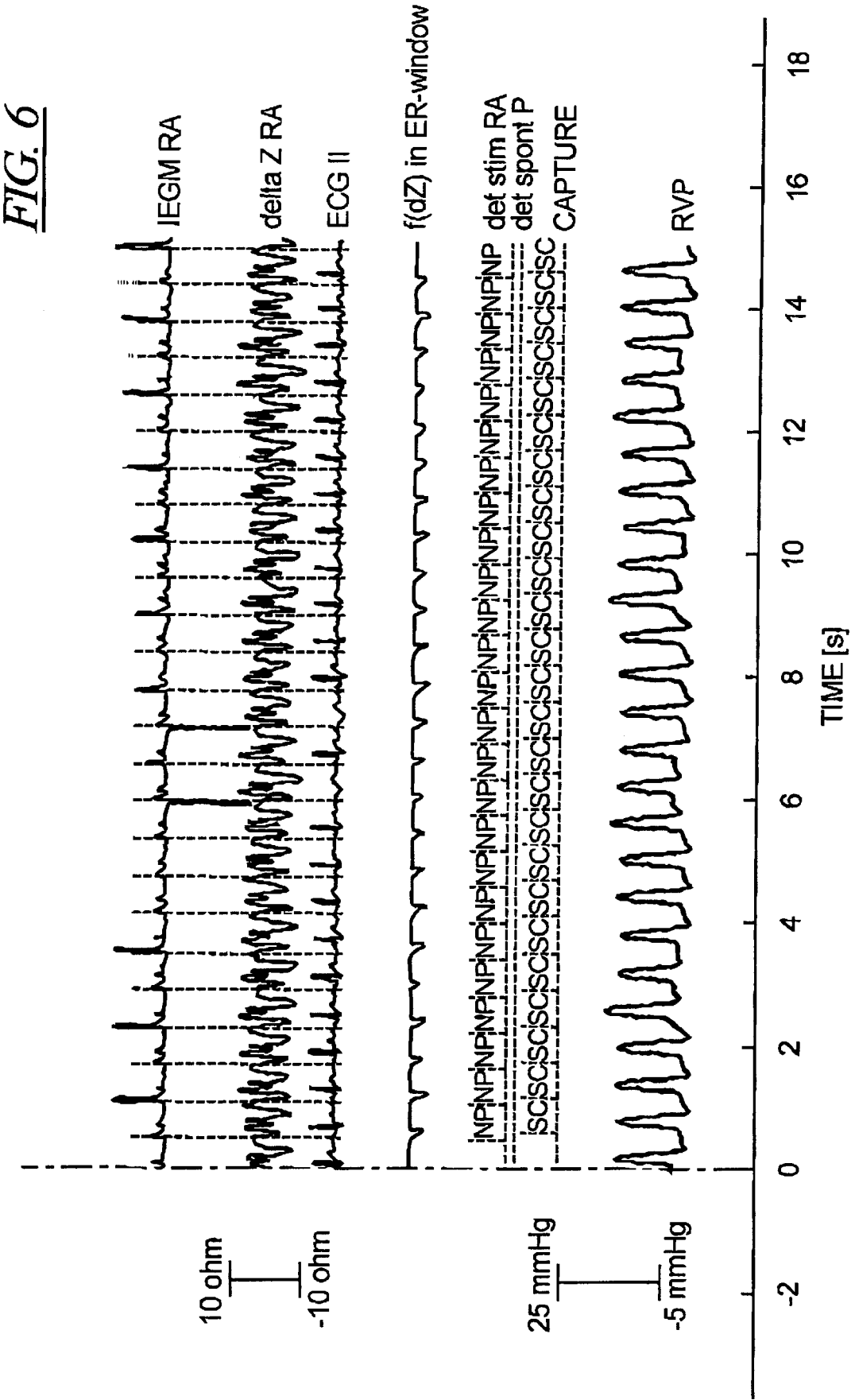
FIG. 6 shows various signal curves obtained in accordance with the invention in a third experimental setup.

FIG. 6 illustrates an overdrive situation, wherein the right atrium is stimulated at a rate higher than the spontaneous rate. The same designations apply as explained in connection with FIG. 7.

Although modifications and changes maybe suggested by those skilled in the art, it is in the intention of the inventor to embody within the patent warranted hereon all changes and modifications as reasonably and properly come within the scope of his contribution to the art.

I claim as my invention:

1. A method for detecting an evoked response in a heart following stimulation of said heart by a stimulation pulse, comprising the steps of:
    defining a time window following emission of a stimulation pulse to a right atrium of a heart;
    in said time window, detecting impedance in said right atrium and thereby obtaining an impedance signal; and
    comparing a characteristic of said impedance signal to a predetermined criterion to obtain a comparison result indicative of whether said stimulation pulse has or has not produced an evoked response in the right atrium.

2. A method as claimed in claim 1 comprising the additional step of high pass filtering said impedance signal to obtain a high pass filtered impedance signal, and comparing said high pass filtered impedance signal to said predetermined criterion.

3. A method as claimed in claim 2 comprising integrating said high pass filtered impedance signal to obtain an integrated high pass filtered impedance signal, and comparing said integrated high pass filtered impedance signal to said predetermined criterion.

4. A method as claimed in claim 3 comprising comparing said integrated high pass filtered impedance signal to a threshold as said predetermined criterion.

5. A method as claimed in claim 2 comprising administering a pacing regimen to said heart, which includes said stimulation pulse, and wherein the step of high pass filtering said impedance signal comprises high pass filtering said impedance signal with a bandwidth selected dependent on said regimen.

6. A method as claimed in claim 1 comprising comparing an amplitude of said impedance signal, as said characteristic, to a predetermined threshold as said predetermined criterion.

7. A method as claimed in claim 1 comprising administering a pacing regimen to said heart, which includes said stimulation pulse, and selecting said time window dependent on said pacing regimen.

8. A method as claimed in claim 1 comprising administering a pacing regimen to said heart, which includes said stimulation pulse, and wherein the step of high pass filtering said impedance signal comprises high pass filtering said impedance signal at a bandwidth, and further comprising selecting said time window and said bandwidth dependent on said pacing regimen.

9. A method as claimed in claim 8 comprising selecting said time window to begin 40 ms after said stimulation pulse and to end 160 ms after said stimulation pulse, and selecting said bandwidth as 2–40 Hz.

10. A method as claimed in claim 8 comprising selecting said time window to begin 80 ms after said stimulation pulse and to end 180 ms after said stimulation pulse, and selecting said bandwidth as 4–40 Hz.

11. A method as claimed in claim 1 wherein the step of comparing a characteristic of said impedance signal to a predetermined criterion comprises comparing a morphology of said impedance signal to a predetermined morphology.

12. A method as claimed in claim 11 comprising administering a pacing regimen to said heart, which includes said stimulation pulse, and selecting said predetermined morphology from among a plurality of predetermined morphologies dependent on said pacing regimen.

13. An evoked response detector comprising:
    a sense amplifier adapted for electrical interaction with a right atrium of a heart for obtaining an impedance signal in a time window after artificial stimulation of the heart;
    a high pass filter supplied with said impedance signal for high pass filtering said impedance signal to produce a high pass filtered impedance signal; and
    a comparison unit for comparing a characteristic of said high pass filtered impedance signal to a predetermined criterion and for emitting an output signal, dependent on said comparison, indicating whether an evoked response in the right atrium has or has not occurred in said time window.

14. An evoked response detector as claimed in claim 13 further comprising an integrator connected between said high pass filter and said comparison unit, said integrator integrating said high pass filtered impedance signal to generate an integrated, high pass filtered impedance signal, and said comparison unit comparing said integrated, high pass filtered impedance signal to said predetermined criterion.

15. An evoked response detector as claimed in claim 14 wherein said comparison unit is a threshold detector for comparing said integrated high pass filtered impedance signal to a predetermined threshold.

16. An evoked response detector as claimed in claim 13 wherein said characteristic of said impedance signal is an amplitude of said impedance signal, and wherein said comparison unit is a threshold detector for comparing said amplitude of said impedance signal to a predetermined amplitude threshold.

17. An evoked response detector as claimed in claim 13 wherein said high pass filter has a bandwidth of 2–40 Hz.

18. An evoked response detector as claimed in claim 13 wherein said high pass filter has a bandwidth of 4–40 Hz.

19. An evoked response detector as claimed in claim 13 wherein said characteristic of said impedance signal is a morphology of said impedance signal, and wherein said comparison unit is a morphology comparator for comparing said morphology of said impedance signal to a predetermined morphology.

20. A cardiac pacemaker comprising:
    an electrode lead adapted for electrical interaction with a right atrium of a heart;
    a pulse generator, which generates stimulation pulses, connected to said electrode lead;

pacing logic for controlling said pulse generator to emit said stimulation pulses according to a pacing regimen;

a sense amplifier connected to said electrode lead for measuring impedance via said electrode lead in said right atrium, and connected to said pacing logic to measure said impedance in a time window, set by said pacing logic, following each stimulation pulse, to generate an impedance signal in said time window;

a high-frequency filter supplied with said impedance signal for producing a high-frequency filtered impedance signal; and a comparison unit supplied with said high-frequency filtered impedance signal for comparing a characteristic of said high-frequency filtered impedance signal to a predetermined criterion to obtain a comparison result indicative of whether an evoked response in the right atrium has or has not occurred in said time window, said comparison unit supplying said comparison result to said pacing logic.

21. A pacemaker as claimed in claim 20, wherein said electrode lead has a tip electrode and a ring electrode, and wherein said sense amplifier measures said impedance signal between said tip electrode and said ring electrode.

22. A pacemaker as claimed in claim 21 further comprising an integrator for integrating said high pass filtered impedance signal to obtain an integrated high pass filtered impedance signal, and wherein said comparison unit compares said integrated high pass filtered impedance signal to said predetermined criterion.

23. A pacemaker as claimed in claim 22 wherein said comparison unit compares said integrated high pass filtered impedance signal to a threshold as said predetermined criterion.

24. A pacemaker as claimed in claim 20 further comprising a high pass filter for high pass filtering said impedance signal to obtain a high pass filtered impedance signal, and wherein said comparator unit compares said high pass filtered impedance signal to said predetermined criterion.

25. A pacemaker as claimed in claim 20 wherein said comparison unit compares an amplitude of said impedance signal, as said characteristic, to a predetermined threshold as said predetermined criterion.

26. A pacemaker as claimed in claim 20 wherein said pacing logic sets said time window dependent on said pacing regimen.

27. A pacemaker as claimed in claim 20 wherein said pacing logic is connected to said high pass filter and sets a bandwidth in said high pass filter dependent on said regimen for high pass filtering said impedance signal.

28. A pacemaker as claimed in claim 20 wherein said pacing logic is connected to said high pass filter and sets a bandwidth in said high pass filter for high pass filtering said impedance signal, and selects said time window, dependent on said pacing regimen.

29. A pacemaker as claimed in claim 28 wherein said pacing logic selects said time window to begin 40 ms after said stimulation pulse and to end 160 ms after said stimulation pulse, and sets said bandwidth as 2–40 Hz.

30. A pacemaker as claimed in claim 28 wherein said pacing logic selects said time window to begin 80 ms after said stimulation pulse and to end 180 ms after said stimulation pulse, and sets said bandwidth as 4–40 Hz.

31. A pacemaker as claimed in claim 20 wherein said comparison unit compares a morphology of said impedance signal, as said characteristic to a predetermined morphology, as said predetermined criterion.

32. A pacemaker as claimed in claim 31 further comprising a memory in which a plurality of predetermined morphologies are stored, said memory being connected to said comparison unit and to said pacing logic, and wherein said pacing logic selects one of said predetermined morphologies, dependent on said pacing regimen, for supply from said memory to said comparison unit, for use in said comparison unit as said predetermined criterion.

* * * * *